(12) United States Patent
Asogawa et al.

(10) Patent No.: US 8,013,180 B2
(45) Date of Patent: Sep. 6, 2011

(54) METHOD FOR IMMOBILIZING COMPOUND ONTO COLUMN CARRIER

(75) Inventors: Minoru Asogawa, Tokyo (JP); Toru Matsumoto, Tokyo (JP)

(73) Assignee: NEC Corporation, Tokyo (JP)

( * ) Notice: Subject to any disclaimer, the term of this patent is extended or adjusted under 35 U.S.C. 154(b) by 212 days.

(21) Appl. No.: 12/209,956

(22) Filed: Sep. 12, 2008

(65) Prior Publication Data
US 2009/0076300 A1  Mar. 19, 2009

(30) Foreign Application Priority Data
Sep. 14, 2007 (JP) ................................. 2007-239228

(51) Int. Cl.
*C07C 303/00* (2006.01)
(52) U.S. Cl. ........................................................ 560/17
(58) Field of Classification Search .................. None
See application file for complete search history.

(56) References Cited

U.S. PATENT DOCUMENTS
2005/0202034 A1* 9/2005 Rasmussen et al. ....... 424/185.1

FOREIGN PATENT DOCUMENTS
| JP | 326964 A | | 2/1991 |
| JP | 772132 A | | 3/1995 |
| JP | 2002-098679 A | * | 4/2002 |
| JP | 200298679 A | | 4/2002 |
| JP | 2002529714 A | | 9/2002 |
| JP | 2005164285 A | | 6/2005 |

OTHER PUBLICATIONS

Means et al, Biochemistry, Reactions of 2, 4, 6-Trinitrobenzenesulfonate Ion with Amines and Hydroxide Ion, 1972, 11(19), pp. 3564-3571.*
Sanford et al, Photoactivable Cross-Linked Polyacrylamide for the Site-Selective Immobilization of Antigens and Antibodies, 1998, 10, pp. 1510-1520.*

* cited by examiner

*Primary Examiner* — Paul A Zucker
(74) *Attorney, Agent, or Firm* — Sughrue Mion, PLLC

(57) ABSTRACT

It is intended to provide a method for immobilizing, onto a column carrier, a compound having a sulfo group or a compound to which a sulfo group can be added. The method comprises immobilizing the compound onto the column carrier using a linker comprising: a sulfo group-binding group capable of forming a bond with the sulfo group in the compound; and a carrier-binding group capable of forming a bond with a group present on the surface of the column carrier.

4 Claims, 3 Drawing Sheets

(a)

(b)

METHOD FOR IMMOBILIZING COMPOUND ONTO COLUMN CARRIER

BACKGROUND OF THE INVENTION

1. Field of the Invention

The present invention relates to a method for immobilizing a compound onto a column carrier. The present invention also relates to a method for producing a compound-immobilized carrier and an analysis apparatus using the same.

2. Description of the Related Art

With the development of techniques in recent years, protein- or compound-immobilized carriers have been developed. Apparatuses for separating and analyzing proteins or compounds using these carriers have been developed.

For example, a method using a conventional polystyrene carrier described in Patent Document 1 involves introducing a sulfo group into polystyrene for immobilizing a protein onto a carrier.

Furthermore, Patent Document 2 discloses that a cyclic phenol sulfide is immobilized onto a carrier by physical absorption. A column for analyzing a metal ion is prepared by using the high affinity of the cyclic phenol sulfide for a metal ion.

Furthermore, Patent Document 3 discloses that a bipolarly charged compound is immobilized onto a carrier using physical adsorption based on hydrophobicity for analyzing a component contained in saliva.

Furthermore, Patent Document 4 discloses that a sulfo group is introduced into a carrier by the action of alkylsulfonic acid, and a zwitterionic non-aromatic group is immobilized onto the carrier by a covalent bond with the sulfo group.

[Patent Document 1] Japanese Patent Laid-Open No. 2005-164285
[Patent Document 2] Japanese Patent Laid-Open No. 2002-098679
[Patent Document 3] Japanese Patent Laid-Open No. 7-72132
[Patent Document 4] National Publication of International Patent Application No. 2002-529714

However, the immobilization methods disclosed in these Patent Documents have some problems.

The problem of the immobilization method described in Patent Document 1 is that this immobilization method can immobilize proteins but it is not applicable to many compounds.

The problem of the immobilization methods described in Patent Documents 2 and 3 is that the immobilization methods are not applicable to many compounds. This is because not all compounds have a high physical affinity for the carrier and also because the physical adsorption mechanism using hydrophobicity is not always used. This is further because most commercially available conventional column carriers can only bind to a compound having amino, thiol, carboxyl, or hydroxy groups.

The second problem is that a group having a high affinity for a column carrier is sometimes difficult to introduce into a compound. For example, a well known method for directly attaching a "carboxyl group" to a compound uses a Grignard reagent. However, this method requires several steps and is complicated.

The method described in Patent Document 4 involves introducing a sulfo group into a conventional column carrier by reacting with alkylsulfonic acid and thereby modifying the properties of the carrier to have the ability to bind to an amino group, while modifying the properties of the carrier to form a zwitterionic non-aromatic group. However, this method of only the sulfo group does not solve the problems mentioned above. Moreover, this method is not applicable to those having no ability to bind to a zwitterionic non-aromatic group.

Thus, an object of the present invention is to provide a method for immobilizing, onto a column carrier, a compound having a sulfo group or a compound to which a sulfo group can be added.

SUMMARY OF THE INVENTION

Thus, a compound immobilization method according to the present invention is
a compound immobilization method for immobilizing a compound onto a column carrier wherein the compound having a sulfo group, comprises
immobilizing the compound onto the column carrier using a linker comprising: a sulfo group-binding group capable of forming a bond with the sulfo group in the compound; and a carrier-binding group capable of forming a bond with a group present on the surface of the column carrier.

Moreover, the compound immobilization method according to the present invention, comprises:
binding the sulfo group in the compound with the sulfo group-binding group in the linker; and
binding the carrier-binding group in the linker with the group present on the surface of the column carrier.

Moreover, it is preferred that the sulfo group-binding group should be an amino group.

As well, it is preferred that the linker should be an amino acid.

Also, it is preferred that the carrier-binding group should be a carboxy, thiol, or hydroxy group.

In addition, the compound having a sulfo group may be produced by adding a sulfo group to a compound free from a sulfo group.

According to the present invention, a compound having a sulfo group can be bound onto a column carrier via a linker, even when the compound cannot be immobilized directly onto the column carrier by a chemical bond method.

Moreover, even a compound free from a sulfo group can be immobilized onto a column carrier via a linker by adding a sulfo group to the compound.

DETAILED DESCRIPTION OF THE PREFERRED EMBODIMENTS

Figure 1:
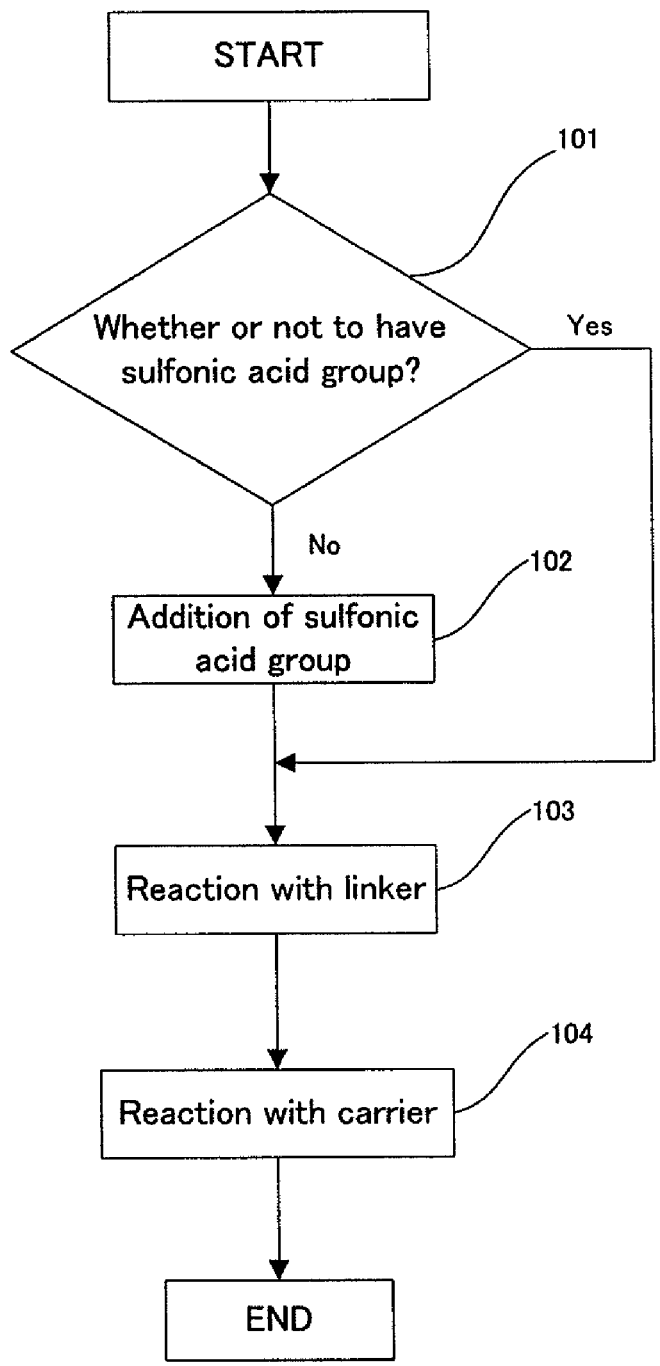
FIG. 1 is a flow chart showing one example of an embodiment of the present invention.

The present invention relates to a method for immobilizing a compound having a sulfo group onto a column carrier. Specifically, the compound immobilization method according to the present invention comprises
binding a compound having a sulfo group to a column carrier using a linker, wherein
the linker comprises: a sulfo group-binding group capable of forming a bond with the sulfo group in the compound; and a carrier-binding group capable of forming a bond with a group present on the surface of the column carrier.

In the present invention, a compound used as the linker has a carrier-binding group capable of forming a bond with a group present on the surface of the column carrier and has a sulfo group-binding group capable of forming a bond with the sulfo group. As a result, a compound having a sulfo group can be bound to a column carrier via the linker, even when the compound having a sulfo group cannot be immobilized directly onto the column carrier by a chemical bond method.

Embodiment 1

In the immobilization method for a compound having a sulfo group according to the present invention, a bond is firstly formed between the sulfo group in the compound and the sulfo group-binding group in the linker. Next, a bond is formed between the carrier-binding group in the linker and the group present on the surface of the column carrier to immobilize the compound having a sulfo group onto the column carrier via the linker.

In the present invention, the compound having a sulfo group may be any compound having therein a sulfo group as a substituent. In Particular, it is preferred for the application of the immobilization method according to the present invention that the compound having a sulfo group should have an aromatic ring and have at least one sulfo group as a substituent in this aromatic ring.

In the present invention, the linker that can be used is a compound that has a sulfo group-binding group capable of forming a bond with the sulfo group in the compound and that has a carrier-binding group capable of forming a bond with a group present on the surface of the column carrier (hereinafter, also referred to as the carrier surface). Examples of the sulfo group-binding group can include an amino group. Moreover, the carrier-binding group is not particularly limited and can be, for example, a carboxy group for an amino group used as the group present on the carrier surface. Alternatively, the carrier-binding group can be, for example, an amino group for a carboxyl group used as the group present on the carrier surface.

For example, specific examples of the linker for an amino group used as the group present on the carrier surface can include an amino acid. In this case, the amino group in the amino acid can form a bond with the sulfo group in the compound, while the carboxy group in the amino acid can form a bond with the amino group present on the carrier surface to thereby immobilize the compound having a sulfo group onto the column carrier.

The column carrier that can be used in the present invention is any carrier having a modifying group on the surface. Examples of the modifying group can include a hydrocarbon having a functional group. Examples of a hydrocarbon include saturated or unsaturated hydrocarbons such as aliphatic, aromatic, and alicyclic hydrocarbons. Examples of the functional group can include amino, carboxy, thiol, nitrile, and hydroxy groups. This functional group forms a bond with the carrier-binding group in the linker. Examples of the carrier include, but are not particularly limited to, porous carriers such as silica gel, diatomaceous earth, alumina, and powder zeolite.

The bond between the compound having a sulfo group and the sulfo group-binding group in the linker can be formed by a conventional method. For example, a covalent bond can be formed by reaction between the sulfo group in the compound and with the amino group in the linker, but is not particularly limited thereto. This reaction can be performed under mild conditions.

A method for binding the carrier-binding group in the linker with the group present on the carrier surface is not particularly limited and can be selected appropriately from conventional methods according to the types of the carrier-binding group in the linker and the group present on the carrier surface. A peptide bond can be formed by condensation reaction, for example, between an amino group used as the group present on the carrier surface and a carboxy group used as the carrier-binding group in the linker.

Embodiment 2

The compound immobilization method according to the present invention can also be applied to the immobilization of a compound free from a sulfo group by adding a sulfo group to the compound free from a sulfo group. The phrase "adding a sulfo group" used herein also encompasses converting a substituent present in the compound free from a sulfo group to a sulfo group.

In this case, the compound free from a sulfo group is preferably a low-molecular-weight compound that has a molecular weight in the order of 50 to 1000, more preferably a compound that has a molecular weight in the order of 100 to 400. A compound having a molecular weight smaller than 50 tends to be too highly reactive, and it sometimes happen that the addition of a sulfo group to the compound is more difficult and the yields are reduced. A compound having a molecular weight larger than 1000 tends to be low reactive, and it sometimes happen that the addition of a sulfo group to the compound is more difficult. Moreover it may occur that solvents that can be used in the reaction are limited. The compound free from a sulfo group is preferably a compound to which a sulfo group can be added without destroying the main skeleton.

A method for adding a sulfo group to the compound that can be used is not particularly limited and is any method known in the art. Specific examples thereof include a method described in Patent Document 2, comprising adding a sulfo group using a sulfuric acid solution. Alternatively, for example, a thiol, disulfide, or sulfinic acid compound can be converted to a compound having a sulfo group through oxidation with permanganate or the like. Alternatively, a sulfo group can be added to the compound through electrophilic substitution reaction using fuming sulfuric acid or chlorosulfuric acid. In this case, the compound of interest can be synthesized at low cost.

Next, the embodiments of the present invention will be described in detail with reference to the drawings.

FIG. 1 shows a method for immobilizing a compound onto a carrier as an embodiment of the present invention.

In the step 101 of FIG. 1, whether or not a compound to be immobilized has a sulfo group is determined. When the compound to be immobilized does not have a sulfo group, the procedure of adding a sulfo group to the compound is performed in step 102. A method for adding a sulfo group to the compound that can be used is not particularly limited and is any method known in the art.

In step 103, the compound having a sulfo group is reacted with a sulfo group-binding group (e.g., an amino group) in the linker. Alternatively, the sulfo group in the compound to which the sulfo group has been added is reacted with the sulfo group-binding group (e.g., an amino group) in the linker. This reaction can be performed using a technique known in the art and can be allowed to proceed under relatively mild conditions.

In step 104, a carrier-binding group in the linker is bound with the group present on the carrier surface.

In the present invention, a compound having a sulfo group or a compound to which a sulfo group can be added can be immobilized onto a carrier by the presence of the linker. Thus, an analysis apparatus using the compound-immobilized column can be provided.

In this context, the present invention has a wider variety of linkers to choose from and has the advantage that many compounds can be used as the linker. For example, the linker that can be used is an amino acid or protein having amino and carboxyl groups.

Moreover, the embodiments of the present invention can adopt a relatively mild reaction step, and therefore have the advantage that the chemical properties of the compound to be immobilized or the linker are less likely to be impaired.

Moreover, in the embodiments of the present invention, the linker can be firstly bound with the column carrier and then the compound having a sulfo group can react with the linker to form a bond. Thereby, the compound having a sulfo group can be immobilized onto the column carrier. The constitution for achieving this purpose is shown in FIG. 2.

Figure 2:
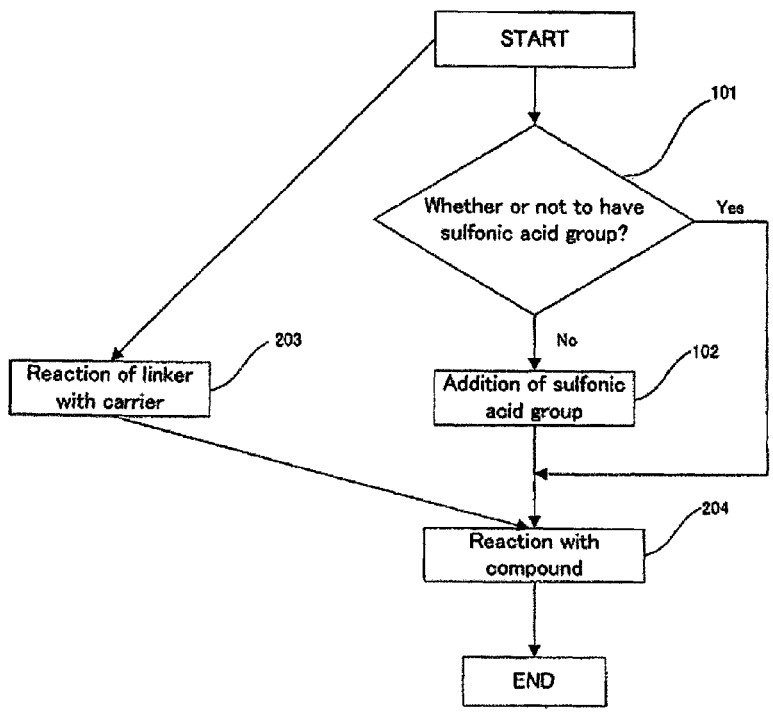
FIG. 2 is a flow chart showing one example of an embodiment of the present invention.

In the embodiment shown in FIG. 2, the carrier-binding group in the linker reacts with the group present on the carrier surface to form a bond, as shown in step 203. In step 204, the sulfo group in the compound to be immobilized reacts with the sulfo group-binding group in the linker to form a bond. Thus, the present invention produces the effect of expanding the range of choices in each immobilization condition.

Figure 3:
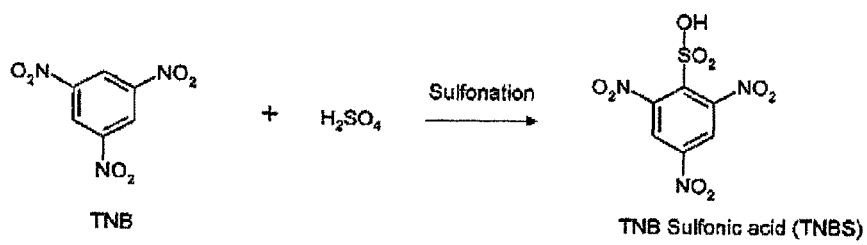
FIG. 3 shows a reaction formula, when the present invention is applied to TNB immobilization.
Figure 3:
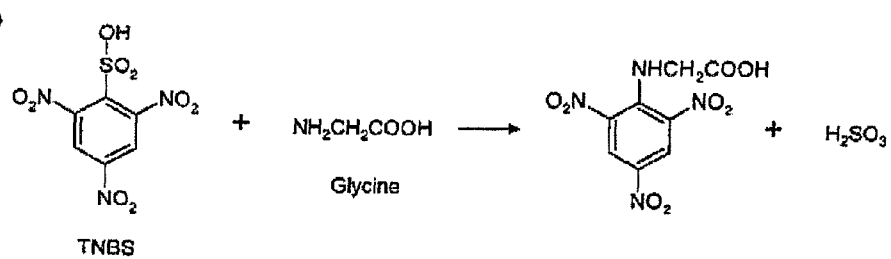

FIG. 3 shows a reaction formula, when trinitrobenzene (hereinafter, abbreviated to TNB) as an example is immobilized onto a column carrier using the present invention.

EXAMPLES

Hereinafter, the present invention will be described with reference to Examples. However, the present invention is not particularly intended to be limited to these Examples.

Example 1

Preparation of TNBS Column Carrier

Example will be shown wherein trinitrobenzenesulfonic acid (hereinafter, abbreviated to TNBS) selected as a low-molecular-weight compound having a sulfo group was immobilized on a column carrier using glycine as a linker. In addition, TNBS can be produced easily from TNB through the reaction described in FIG. 3(a).

First, TNBS was dissolved in dimethyl sulfoxide (hereinafter, abbreviated to DMSO) to prepare a 0.1 mM TNBS solution. Glycine used as a linker was also dissolved in a 0.5 mM phosphate buffer to prepare a 0.1 mM glycine solution.

Next, both the solutions were mixed in equal amounts and the mixture was left at 4° C. for 24 hours, followed by reaction (at room temperature). The pH of this mixed solution was 4.5. This reaction can be allowed to proceed relatively mildly.

Figure 4:
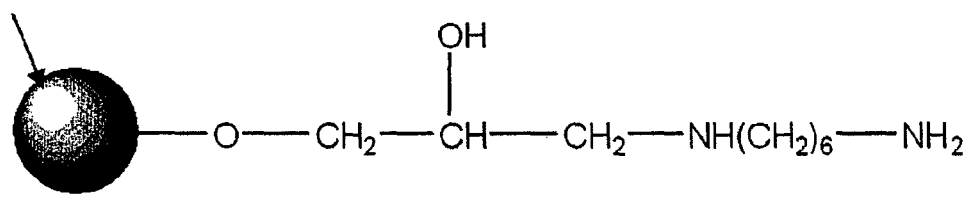
FIG. 4 is a diagram showing the structure of EAH Sepharose 4B manufactured by GE Healthcare Bioscience.

The column carrier used was EAH Sepharose 4B (trade name; manufactured by GE Healthcare Bioscience). The structure of this column carrier is shown in FIG. 4.

In addition, an amino group in this column carrier shows little reactivity. Therefore, the column carrier, as described later, was activated with 1-ethyl-3-(3-dimethylaminopropyl) carbodiimide and then subjected to Examples and Comparative Examples of the present application.

Next, ethanol was removed from the column carrier using a glass filter. The resulting carrier was added at a concentration of 1 w/v % to the solution prepared as mentioned above. Moreover, 1-ethyl-3-(3-dimethylaminopropyl)carbodiimide (hereinafter, abbreviated to EDC) was added thereto as an activator. The mixture was shielded from light and left at room temperature for 24 hours to form a peptide bond between the amino group in the column carrier and the carboxy group in glycine bound with TNBS.

Next, the column carrier was collected using a glass filter and well washed with pure water and then with a glycine solution of pH 2.3. Next, the column carrier was washed with pure water and then with an 8 M Urea/phosphate buffer. Next, the column carrier was washed with a phosphate buffer and next with a carbonate buffer of pH 9.5. Finally, the column carrier was washed with pure water.

TNBS was immobilized on the column carrier using the linker through this treatment to obtain a TNBS column carrier.

(Preparation of TNBS-AP)

An aptamer specifically binding to TNBS (hereinafter, abbreviated to TNBS-AP) was prepared as described below. In addition, the aptamer was prepared with reference to Non-Patent Document 1 (Fitzwater and Polisky. (1996) Meth. Enz. 267: 275-301) and Patent Document 5 (National Publication of International Patent Application No. 2003-517295).

Two DNA oligonucleotides (40 N R0 DNA template and 5' N7 primer) were annealed and filled in with Klenow to produce a 40 N R0 DNA transcription template. This DNA oligonucleotide that was used was manufactured by Operon (Minneapolis, Minn., USA). This template was transcribed using T7 RNA polymerase, 3 mM 2-F uridine, 3 mM cytosine, 1 mM 2'-OH guanosine, 1 mM adenine, and αP-ATP, as described in Non-Patent Document 1. The T7 RNA polymerase that was used was manufactured by Enzyco (Denver, Colo., USA). All the restriction enzymes that were used were manufactured by New England Biolabs. This resulted in a R0 40 N7 nucleic acid pool having 5' and 3' "fixed" regions and a 40 base long random sequence region.

Next, the previously obtained TNBS column carrier was incubated with this nucleic acid pool together with a Dulbecco's phosphate-buffered saline and 1 mM magnesium chloride. Next, the TNBS column carrier was washed under the conditions shown in Table 3 of Patent Document 5.

Next, the TNBS column carrier was treated with 50% ethanol and 4 M urea at 65° C. for 45 minutes to elute the aptamer. Then, the aptamer was precipitated with ethanol to obtain TNBS-AP.

Next, the TNBS-AP was reverse-transcribed using avian myeloblastosis virus reverse transcriptase and subjected to polymerase chain reaction (PCR) using 5' N7 and 3' N7 primers for 15 cycles.

The obtained transcription template was transcribed with T7 RNA polymerase in the presence of 2'-F pyrimidine nucleotides, 2'-OH purine ribonucleotides, and α32P-ATP, and carried to the next spot round. Nine rounds in total were performed to select TNBS-AP.

The binding force between the TNBS-AP obtained by the treatment mentioned above and the TNBS was measured with a surface plasmon resonance biosensor. Specifically, the surface plasmon resonance (SPR) was measured to determine the degree of binding strength between the TNBS and the TNBS-AP. The surface plasmon resonance biosensor that was used was Biacore 3000 (trade name; manufactured by Biacore). A chip for TNBS-AP immobilization that was used was Sensor Chip CM5 (trade name; manufactured by Biacore). The aptamer was immobilized by a method comprising: NHS-activating a carboxyl group in carboxymethyldextran on the surface of the chip (Sensor Chip CM5) by reaction with an NHS/EDC mixed solution and by binding the NHS-activated carboxyl group to the TNBS-AP. Subsequently, the residual active NHS group was blocked with ethanolamine to complete immobilization (NHS represents N-hydroxysuccinimide). The binding state was evaluated by reaction with a TNBS solution after TNBS-AP immobilization on the CM5 chip. The results are shown in Table 1.

Comparative Example 1

As a Comparative Example, low-molecular-weight compounds free from a sulfo group, that is, TNB, trinitrophenol (TNP), trinitrotoluene (TNT), and trinitrobenzene carboxylic acid (TNBC), were immobilized on column carriers in the same way as in Example 1.

In this immobilization method, the compounds were independently immobilized instead of TNBS of Example 1, and the obtained carriers were respectively referred to as TNB, TNP, TNT, and TNBC column carriers.

Moreover, the aptamer selection for each compound was performed in the same way as in Example 1, and the obtained aptamers were respectively referred to as TNB-AP, TNP-AP, TNT-AP, and TNBC-AP.

The binding force between the prepared aptamers and their corresponding compounds was evaluated. The results are shown in Table 1.

Comparative Example 2

As a Comparative Example, an aptamer that was selected using a column carrier reacted with TNBS without use of a linker was referred to as Cont-TNBS-AP. The affinity value between the TNBS and the Cont-TNBS-AP was 1. This is probably because an aptamer was hardly selected due to little immobilization of the TNBS on the column carrier.
(Result Comparison 1)

As shown in Table 1, a strong affinity (bond) was observed between TNBS and TNBS-AP. When this affinity value between TNBS and TNBS-AP was defined as 100, the affinity values between other compounds and their corresponding aptamers were calculated. As a result, the affinity value between TNBC and TNBC-AP was 20, 5 between TNP and TNP-AP, 1 between TNT and TNT-AP, and 0 between TNB and TNB-AP.

The TNBS column carrier exhibited a strong affinity for TNBS-AP. This is probably because an aptamer binding to TNBS could be selected by virtue of the strong immobilization of the TNBS on the column carrier via the linker.

On the other hand, TNB, TNP, TNT, and TNB did not produce a sufficient affinity for their corresponding aptamers. This is probably because an aptamer binding to each compound was not selected due to the insufficient immobilization of these chemical substances onto the columns. This insufficient immobilization is probably due to reduction of binding force to the linker associated with acid strength reduced in the sequence of sulfonic acid, carboxylic acid, and phenol.
[Table 1]

Example 2

Example will be shown in which a sulfo group was added to catechin, a tea ingredient, which was selected as a low-molecular-weight compound, which was then immobilized on a column carrier using cysteine as a linker.

First, 1 g of catechin was reacted with stirring slowly in 10 ml of 1 M chlorosulfuric acid, and one hydroxy group in the catechin was sulfonated. Then, the sulfonated catechin (hereinafter, referred to as S-catechin) obtained after purification was dissolved in DMSO to prepare a 0.1 mM S-catechin solution.

Next, cysteine used as a linker was dissolved in a 0.5 phosphate buffer to prepare a 0.1 mM cysteine solution.

The S-catechin solution and the cysteine solution were mixed in equal amounts and the mixture was left at 4° C. for 24 hours, followed by reaction.

The column carrier used was the same as in Example 1. Then, the same treatment as in Example 1 was performed to prepare an S-catechin column carrier.

Subsequently, an aptamer was selected in the same way as in Example 1 using the S-catechin column carrier. The obtained aptamer was referred to as S-catechin-AP.

Then, an affinity between the S-catechin and the S-catechin-AP was evaluated according to Example 1. The results are shown in Table 2.

Comparative Example 3

As a Comparative Example, a catechin as a low-molecular-weight compound free from a sulfo group was immobilized on a column carrier in the same way as in Example 1.

In this immobilization method, the catechin was immobilized instead of S-catechin of Example 2 to prepare a catechin column carrier.

Moreover, aptamer selection was performed in the same way as in Example 1 using the catechin column carrier, and the obtained aptamer was referred to as catechin-AP.

The affinity between the catechin and the catechin-AP was evaluated according to Example 1. The results are shown in Table 2.
(Result Comparison 2)

A strong affinity was observed between S-catechin and S-catechin-AP. This is probably because an aptamer binding to S-catechin could be selected by virtue of the strong immobilization of the sulfonated catechin on the column.

On the other hand, when the affinity value between S-catechin and S-catechin-AP was defined as 100, the affinity value between catechin and catechin-AP was a value as low as 7. This is probably because an aptamer binding to catechin was not selected due to insufficient immobilization of the catechin onto the column. This insufficient immobilization of the catechin onto the column carrier is probably because the catechin has no substituent that binds to the linker.
[Table 2]

TABLE 1

| Affinity value between chemical substance and its aptamer | | | | | |
|---|---|---|---|---|---|
| Chemical substance | TNBS | TNBC | TNP | TNT | TNB |
| Type of aptamer | TNBS-AP | TNBC-AP | TNP-AP | TNT-AP | TNB-AP |
| Affinity value | 100 | 20 | 5 | 1 | 0 |

TABLE 2

| Affinity value between chemical substance and its aptamer that uses cysteine | | |
|---|---|---|
| Chemical substance | Sulfonated catechin | Catechin |
| Type of aptamer | S-Catechin-AP | Catechin-AP |
| Affinity value | 100 | 7 |

Example 3

Example will be shown wherein benzaldehyde sulfonic acid (BAS), a main ingredient of a peach flavor, selected as a low-molecular-weight compound was immobilized on a column carrier using glycine as a linker.

First, BAS was dissolved in DMSO to prepare a 0.1 mM BAS solution. Moreover, glycine was dissolved in a 0.5 mM phosphate buffer to prepare a 0.1 mM glycine solution.

The 0.1 mM BAS solution and the 0.1 mM glycine solution were mixed in equal amounts and the mixture was left at 4° C. for 24 hours, followed by reaction.

The column carrier used was the same as in Example 1. Then, the same treatment as in Example 1 was performed to prepare a BAS column carrier.

Next, an aptamer was selected in the same way as in Example 1 using the BAS column carrier. The obtained aptamer was referred to as BAS-AP.

Then, an affinity between the BAS and the BAS-AP was evaluated according to Example 1. The results are shown in Table 3.

Comparative Example 4

As a Comparative Example, low-molecular-weight compounds free from a sulfo group, that is, carboxybenzaldehyde (CBA), hydroxybenzaldehyde (HBA), and benzaldehyde (BA), were immobilized on column carriers in the same way as in Example 1.

In this immobilization method, the compounds were independently immobilized instead of BAS of Example 3 to prepare CBA, HBA, and BA column carriers.

Moreover, aptamer selection was performed in the same way as in Example 1 using the prepared CBA, HBA, and BA column carriers, and the obtained aptamers were respectively referred to as CBA-AP, HBA-AP, and BA-AP.

An affinity between the prepared compounds and their corresponding compounds was evaluated according to Example 1. The results are shown in Table 3.

(Result Comparison 3)

A strong affinity was observed between BAS and BAS-AP. When this affinity value between BAS and BAS-AP was defined as 100, the affinity value between CBA and CBA-AP was 60, 30 between HBA and HBA-AP, and 3 between BA and BA-AP.

The BAS exhibited a strong affinity for BAS-AP. This is probably because an aptamer specifically binding to BAS could be selected by virtue of the strong immobilization of the BAS on the column via the linker (glycine).

On the other hand, the affinity value was reduced in the sequence of CBA and CBA-AP, HBA and HBA-AP, and BA and BA-AP. This is probably because an aptamer specifically binding to these compounds was not selected due to the absence of the bond between CBA, HBA, and BA and their column carriers via the linker. This absence of the immobilization of these compounds onto the column carriers via the linker is probably due to reduced binding force to the linker associated with acid strength reduced in the sequence of sulfonic acid, carboxylic acid, and phenol.

[Table 3]

TABLE 3

| Affinity value between chemical substance and its aptamer | | | | |
|---|---|---|---|---|
| Chemical substance | BAS | CBA | HBA | BA |
| Type of aptamer | BAS-AP | CBA-AP | HBA-AP | BA-AP |
| Affinity value | 100 | 60 | 30 | 3 |

As applications of the present invention, a compound having a sulfo group or a compound to which a sulfo group can be added can be immobilized on a carrier, which is in turn used as a column. As a result, this column can be used in, for example, an antigen-antibody reaction or aptamer preparation. For example, an antibody or aptamer selection or analysis can be achieved according to the ability or inability to bind to the compound immobilized thereon.

This patent application insists on priority based on Japanese Patent Application No. 2007-239228 filed on Sep. 14, 2007, and all of the disclosure are herein incorporated.

In the above, the present invention was described with reference to exemplary embodiments and examples, but the present invention is not limited to the exemplary embodiments and examples. The constitution and details of the present invention can be subjected to various modifications that those skilled in the art can understand, in the scope of the present invention.

What is claimed is:

1. A method for immobilizing a compound onto a column carrier by using a linker,
    wherein the compound is a sulfonated aromatic compound, and uses an amino acid as the linker,
    the method comprising:
    a first step of forming a bond between the compound and the amino acid by a reaction between a sulfonate group of the compound and an amino group of the amino acid, and,
    a second step of forming a bond between carboxy group of the amino acid and a group present on the surface of the column carrier.

2. The method for immobilizing a compound according to claim 1, wherein the group present on the surface of the column carrier is an amino group.

3. The method for immobilizing a compound according to claim 1, wherein the sulfonated aromatic compound is produced by adding a sulfonate group to an aromatic compound free from a sulfonate group.

4. The method for immobilizing a compound according to claim 3, wherein the aromatic compound free from a sulfonate group has a molecular weight in the order of 50 to 1000.

* * * * *